United States Patent
Sakashita

(10) Patent No.: US 10,667,708 B2
(45) Date of Patent: Jun. 2, 2020

(54) ULTRASOUND DIAGNOSTIC DEVICE

(71) Applicant: Hitachi, Ltd., Tokyo (JP)

(72) Inventor: Hajime Sakashita, Tokyo (JP)

(73) Assignee: HITACHI, LTD., Tokyo (JP)

( * ) Notice: Subject to any disclaimer, the term of this patent is extended or adjusted under 35 U.S.C. 154(b) by 344 days.

(21) Appl. No.: 15/567,394

(22) PCT Filed: Mar. 10, 2016

(86) PCT No.: PCT/JP2016/057512
§ 371 (c)(1),
(2) Date: Oct. 18, 2017

(87) PCT Pub. No.: WO2016/170867
PCT Pub. Date: Oct. 27, 2016

(65) Prior Publication Data
US 2018/0110425 A1 Apr. 26, 2018

(30) Foreign Application Priority Data
Apr. 23, 2015 (JP) .................................. 2015-088491

(51) Int. Cl.
*A61B 8/00* (2006.01)
*A61B 5/0285* (2006.01)
(Continued)

(52) U.S. Cl.
CPC ............ *A61B 5/0285* (2013.01); *A61B 5/026* (2013.01); *A61B 8/06* (2013.01); *A61B 8/065* (2013.01); *A61B 8/0883* (2013.01); *A61B 8/5223* (2013.01)

(58) Field of Classification Search
CPC ... A61B 5/0285; A61B 8/0883; A61B 8/5223; A61B 5/026; A61B 8/06; A61B 8/065
See application file for complete search history.

(56) References Cited

U.S. PATENT DOCUMENTS

| 5,105,816 A | 4/1992 | Shimura et al. |
| 6,558,325 B1 * | 5/2003 | Pang ........................ A61B 8/06 600/443 |

(Continued)

FOREIGN PATENT DOCUMENTS

| JP | H02-305559 A | 12/1990 |
| JP | 2008-000583 A | 1/2008 |

(Continued)

OTHER PUBLICATIONS

International Search Report received for PCT Patent Application No. PCT/JP2016/057512, dated Apr. 26, 2016, 2 pages.

*Primary Examiner* — Joel Lamprecht
(74) *Attorney, Agent, or Firm* — Baker Botts L.L.P.

(57) ABSTRACT

A velocity vector calculating unit 40 obtains velocity vectors at various coordinates in a blood flow, on the basis of signals obtained by transmitting and receiving ultrasonic waves, thereby generating a plurality of vector frames, each formed from velocity vectors at a plurality of coordinates. An interpolation processing unit 50 generates interpolated frames by employing an interpolation process between two adjacent vector frames, and adds one or a plurality of such interpolated frames between said vector frames. The interpolation processing unit 50 generates each interpolated frame, formed from interpolated vectors at a plurality of coordinates, by means of an interpolation process based on velocity vectors between the two adjacent vector frames.

15 Claims, 12 Drawing Sheets

(51) Int. Cl.
 *A61B 8/06* (2006.01)
 *A61B 5/026* (2006.01)
 *A61B 8/08* (2006.01)

(56) References Cited

U.S. PATENT DOCUMENTS

| | | | |
|---|---|---|---|
| 8,150,128 B2 * | 4/2012 | Konofagou | A61B 8/08 382/131 |
| 2010/0249592 A1 * | 9/2010 | Langeland | A61B 8/08 600/443 |
| 2013/0289408 A1 | 10/2013 | Tanaka et al. | |
| 2015/0013471 A1 | 1/2015 | Ono et al. | |

FOREIGN PATENT DOCUMENTS

| | | |
|---|---|---|
| JP | 2008-073279 A | 4/2008 |
| JP | 2013-165922 A | 8/2013 |
| JP | 2013-192643 A | 9/2013 |
| WO | 2012073863 A1 | 6/2012 |

* cited by examiner

ULTRASOUND DIAGNOSTIC DEVICE

CROSS-REFERENCE TO RELATED APPLICATIONS

This application is a national phase claiming the benefit of and priority to International Patent Application No. PCT/JP2016/057512, entitled "ULTRASOUND DIAGNOSTIC DEVICE", filed Mar. 10, 2016, which claims priority to Japanese Patent Application No. 2015-088491, filed Apr. 23, 2015, which are hereby incorporated by reference in their entireties.

TECHNICAL FIELD

The present disclosure relates to an ultrasound diagnostic apparatus, and in particular, to a technique for obtaining movement information of a bloodstream.

BACKGROUND

Techniques are known for obtaining movement information (motion information) of a bloodstream from a reception signal obtained by transmitting and receiving ultrasound to and from a bloodstream. For example, Patent Document 1 discloses a technique in which two-dimensional velocity vectors related to a fluid are obtained at a plurality of points in an observation plane based on a reception signal obtained by transmitting and receiving ultrasound to and from the fluid such as the bloodstream in a living body. It becomes possible to obtain diagnostic information such as a flow line showing a flow of the fluid based on a distribution of the two-dimensional velocity vectors at the plurality of points in the observation plane, and, for example, application to diagnosis of a heart or the like is expected.

Patent Document 2 discloses an ultrasound diagnostic apparatus in which there is formed an image which expresses the bloodstream in the living body as a motion of a plurality of display elements. As each display element, a virtual particle of the bloodstream is desirable, and a device described in Patent Document 2 determines a position (movement destination) of each particle at a next frame based on a velocity vector of the particle in a current frame, and displays, for example, a trajectory or the like of each particle obtained by tracking the movement destination of each particle over a plurality of frames. With such a configuration, for example, it becomes possible to visually and intuitively check a state in the bloodstream such as an eddy flow, a turbulent flow, a stationary state, or the like.

CITATION LIST

Patent Literature

Patent Document 1: JP 2013-192643 A
Patent Document 2: JP 2008-73279 A

SUMMARY

Technical Problem

The techniques of Patent Documents 1 and 2 are highly useful in application when obtaining the movement information (motion information) of the bloodstream, and further application and improvement of these techniques are expected.

The present disclosure has been made in view of the above-described related art, and an advantage thereof lies in improving precision of the movement information of the bloodstream obtained using ultrasound.

Solution to Problem

According to one aspect of the present disclosure, there is provided an ultrasound diagnostic apparatus comprising: a vector calculator that obtains a bloodstream vector at each coordinate in a coordinate system including a bloodstream based on a signal obtained by transmitting and receiving ultrasound, to generate a plurality of vector frames formed from each vector frame including bloodstream vectors at a plurality of coordinates; an interpolation processor that generates each interpolated frame by applying an interpolation process between two vector frames which are adjacent to each other, and that adds one or a plurality of interpolated frames between the vector frames; and a particle calculator that derives a movement destination of each virtual particle of the bloodstream based on a frame array formed from a plurality of vector frames and a plurality of interpolated frames added between the vector frames.

In the above-described configuration, the bloodstream vector is vector information related to a motion of the bloodstream, and is desirably, for example, a velocity vector indicating a velocity and a direction at each coordinate in the bloodstream (each bloodstream part), a movement vector indicating an amount of movement and a direction at each coordinate in the bloodstream, or the like. The bloodstream vector can be obtained, for example, by means of the technique described in Patent Document 1 (JP 2013-192643 A); that is, using a two-dimensional velocity vector distribution, or alternatively, the bloodstream vector may be obtained by means of other known techniques.

The coordinate system in the above-described configuration forms a reference for mathematically (geometrically) expressing the position, the size, and the direction of the bloodstream vector. The coordinate system corresponds to an actual space (region including the bloodstream) to and from which the ultrasound is transmitted and received. For example, typically, the coordinate system is defined with the position of a probe which transmits and receives the ultrasound as a reference (for example, the origin), but alternatively, another position may be set as the reference (origin) of the coordinate system.

Each vector frame is formed by bloodstream vectors at a plurality of coordinates of the coordinate system including the bloodstream. For example, a scanning plane is formed by scanning the ultrasound in a cross section including the bloodstream in the living body, and the scanning planes are repeatedly formed over a plurality of time phases, to form a plurality of vector frames corresponding to the plurality of time phases.

The virtual particle of the bloodstream is a virtual element in the calculation used for analysis of the bloodstream (flow of blood), and, for example, one or a plurality of virtual particles are generated in the bloodstream to be diagnosed.

According to the apparatus of the above-described configuration, a frame array is formed in which a plurality of interpolated frames are added to a plurality of vector frames, and the movement destination of each virtual particle of the bloodstream is derived based on the frame array. Because the frame array is formed by adding the plurality of interpolated frames to the plurality of vector frames, a frame rate of the frame array can be increased as compared to the case where the frame array is formed with only the plurality of vector frames. Further, based on the frame array having the frame rate increased, the movement destination of each virtual particle of the bloodstream is derived. Because of this, an estimation precision of the movement destination can be improved as compared to the case where the frame rate is low.

For example, in a case where, although the bloodstream vector of each particle changes relatively greatly between frames of the plurality of vector frames, if the movement destination of each particle is estimated between the frames without considering the change, there is a possibility that the estimated movement destination and the original movement destination may be significantly deviated from each other.

In particular, when transmission and reception of color Doppler method is used for obtaining the bloodstream vectors at the plurality of coordinates, because the ultrasound is repeatedly transmitted and received to and from a same beam direction, the frame rate is lower as compared to, for example, the case where a B-mode image is obtained. When the movement destination of each particle is estimated between frames including only the plurality of vector frames obtained with the lower frame rate, there is a possibility that the estimated movement destination is significantly deviated from the original movement destination.

In contrast, according to the above-described apparatus, an interpolation process based on the bloodstream vector, for example, is applied between two vector frames which are adjacent to each other, and one or a plurality of interpolated frames are added between the vector frames. The added interpolated frames are desirably formed from the interpolated vectors at a plurality of coordinates, for example. The interpolated vector is obtained by, for example, applying an interpolation process based on the bloodstream vector, and, in the interpolated vector, a change of the bloodstream vector between the vector frames is reflected.

According to the above-described apparatus, the movement destination of each virtual particle of the bloodstream is derived based on the frame array formed by a plurality of vector frames and a plurality of interpolated frames added between the vector frames. The frame array is formed by adding one or a plurality of interpolated frames between two vector frames which are adjacent to each other, and reflects the change of the bloodstream vector between the vector frames.

Therefore, by deriving the movement destination of each particle based on such a frame array, it becomes possible to derive the movement destination of each particle with consideration of the change of the bloodstream vector between the vector frames. With such a configuration, the estimation precision of the movement destination can be significantly improved as compared to the case where the change of the bloodstream vector between the vector frames is ignored or only lightly considered. The above-described apparatus can improve the estimation precision of the movement destination, for example, when the frame rate of the plurality of vector frames is relatively low, and, in addition, the apparatus may handle the needs for further improving the estimation precision of the movement destination even when the frame rate of the plurality of vector frames is not so low.

According to another aspect of the present disclosure, the interpolation processor generates each of the interpolated frames formed from interpolated vectors at the plurality of coordinates by an interpolation process based on the bloodstream vector between two vector frames which are adjacent to each other.

According to another aspect of the present disclosure, the particle calculator calculates, based on the bloodstream vector of each particle in each frame included in the frame array corresponding to a plurality of time phases, a coordinate of the movement destination of the particle in a frame of a time phase later than the frame.

According to another aspect of the present disclosure, the ultrasound diagnostic apparatus further comprises a display processor that forms a bloodstream display image in which the coordinate of the movement destination of the particle over a plurality of time phases is shown in an image.

According to another aspect of the present disclosure, the display processor forms the bloodstream display image in which the coordinate of the movement destination of the particle over the plurality of time phases is shown by a trajectory by at least one of a point and a line.

According to another aspect of the present disclosure, in showing the trajectory of the particles over the plurality of time phases, the display processor sets different display forms between a trajectory portion of a time phase corresponding to a bright display period of the particle and a trajectory portion of a time phase corresponding to a period other than the bright display period. For example, only the trajectory portion corresponding to the bright display period is displayed, or the trajectory portion corresponding to the bright display period is shown with a solid line and the trajectory portion corresponding to the other periods is shown with a broken line. Alternatively, the trajectory portion corresponding to the bright display period is emphasized by a display process such as setting a lower brightness of the trajectory portion corresponding to the periods other than the trajectory portion corresponding to the bright display period, so as to avoid or reduce crowding of the display of the trajectory by the trajectory portion of the other periods.

According to another aspect of the present disclosure, the display processor sets a period from the time phase in which the trajectory of each particle is displayed to a time phase of a predetermined time period in the past as the bright display period of the particle. The predetermine time period (first predetermined time period) may be a fixedly set time period, or may be set by adjustment or selection by a user.

According to another aspect of the present disclosure, the display processor sets a period from the time phase in which each particle is generated to a time phase of a predetermined time period later as the bright display period of the particle. The predetermined time period (second predetermined time period) may be a fixedly set time period, or may be set by adjustment or selection by the user. The second predetermined time period and the first predetermined time period may differ from each other.

According to another aspect of the present disclosure, the ultrasound diagnostic apparatus further comprises: an image former that forms an ultrasound image of a heart including the bloodstream based on the signal obtained by transmitting and receiving ultrasound; and a particle generator that generates a plurality of virtual particles of the bloodstream on a generation line connecting two characteristic points in the ultrasound image.

According to another aspect of the present disclosure, the two characteristic points are moved to follow a change of a shape of the heart in the ultrasound image formed over the plurality of time phases, so that the generation line follows a motion of the heart over the plurality of time phases.

Advantageous Effects of Invention

According to various aspects of the present disclosure, precision of movement information of the bloodstream obtained using the ultrasound is improved. For example, according to an embodiment of the present disclosure, a frame array in which a plurality of interpolated frames are added to a plurality of vector frames is formed, and a movement destination of each virtual particle of the bloodstream is derived based on the frame array. Thus, the estimation precision of the movement destination can be significantly improved as compared to a case where the change of the bloodstream vector between vector frames is ignored or only lightly considered.

DESCRIPTION OF EMBODIMENTS

Figure 1:
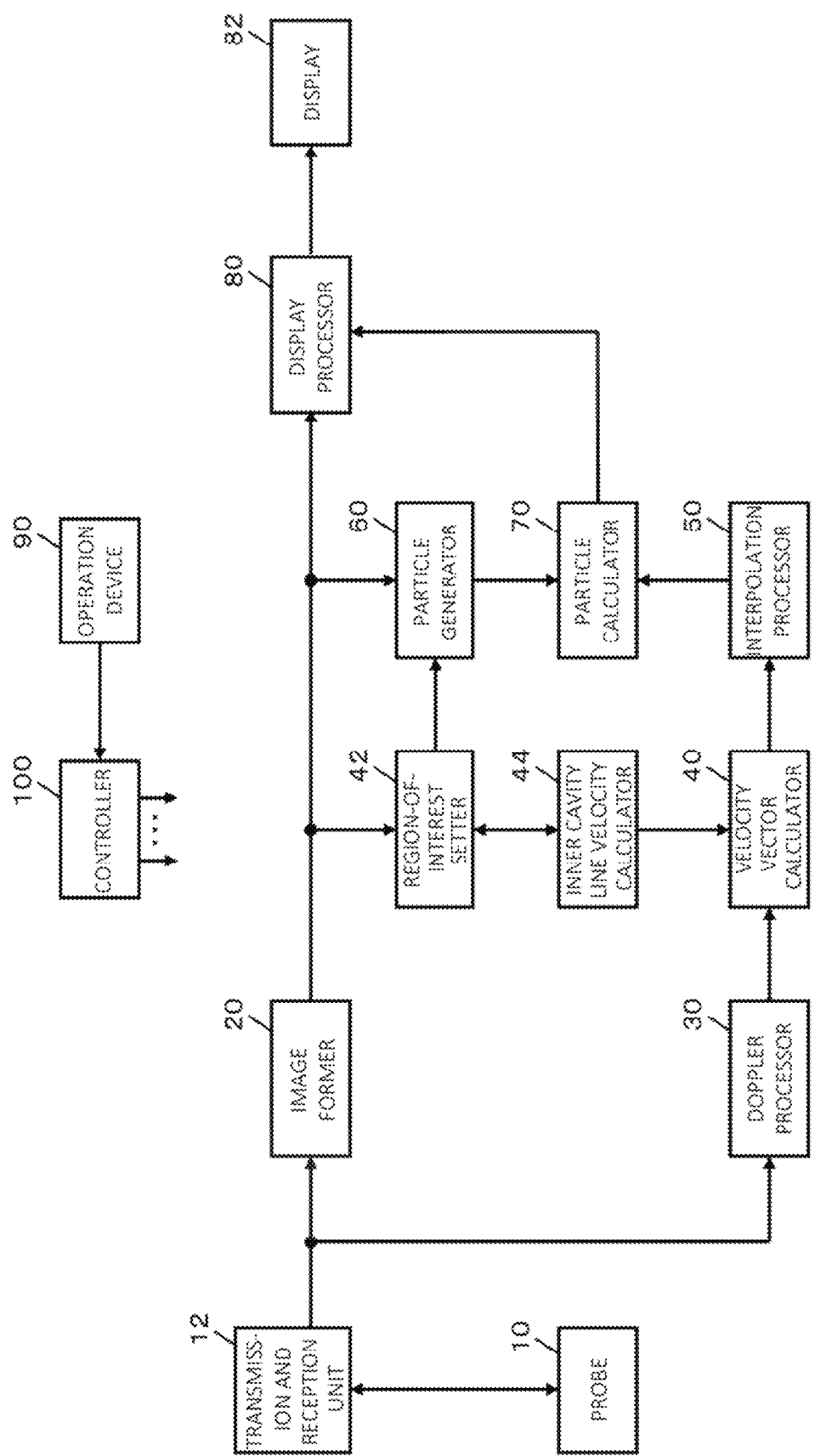
FIG. 1 is a diagram showing an overall structure of an ultrasound diagnostic apparatus desirable in the present disclosure.

FIG. 1 is an overall structural diagram of an ultrasound diagnostic apparatus desirable in the present disclosure. The ultrasound diagnostic apparatus shown in FIG. 1 has a function to obtain movement information of a bloodstream (flow of blood), and in particular, is desirable for diagnosis of the bloodstream in a heart of a living body. Alternatively, a bloodstream other than that in the heart may be set as a diagnosis target.

A probe 10 is an ultrasound probe which transmits and receives ultrasound to and from a region including a diagnosis target such as, for example, the heart in the living body. The probe 10 has a plurality of transducer elements, which are electrically scan-controlled, to scan an ultrasound beam in a space including the heart. For example, the probe 10 is held by a user (inspector) such as a doctor, and is used in contact with a body surface of a subject. The probe 10 may be a probe which is used while being inserted into a body cavity of the subject, or a probe in which the electronic scan and a mechanical scan are combined. As the probe 10, for example, a convex-type probe is desirable, but alternatively, the probe 10 may be of a sector type, a linear type, or the like.

A transmission and reception unit 12 has functions as a transmission beam former and a reception beam former. Specifically, the transmission and reception unit 12 forms a transmission beam by outputting a transmission signal to each of the plurality of transducer elements of the probe 10, and further, forms a reception beam by applying a phasing addition process or the like to a plurality of reception wave signals obtained from the plurality of transducer elements. With such a process, an ultrasound beam (the transmission beam and the reception beam) is scanned in a scanning plane, and a reception signal corresponding to the ultrasound beam is formed. In obtaining the reception signal of the ultrasound, the ultrasound beam may be three-dimensionally scanned in a three-dimensional space, or a technique such as transmission aperture synthesis may be employed.

An image former 20 forms data of an ultrasound image (image data) based on the reception signal of the ultrasound obtained from within the scanning plane. The image former 20 applies processes such as, for example, a wave detection process, a filter process, and an A/D conversion process on the reception signal of the ultrasound, to form frame data for a B-mode image. Alternatively, image data related to known ultrasound images other than the B-mode image may be formed.

A Doppler processor 30 measures an amount of Doppler shift included in the reception signal corresponding to the ultrasound beam. The Doppler processor 30 measures the Doppler shift caused in the reception signal of the ultrasound by the bloodstream by, for example, a known Doppler process, and obtains velocity information (Doppler information) of an ultrasound beam direction for the bloodstream.

A velocity vector calculator 40 forms a distribution of a two-dimensional velocity vector in the scanning plane, based on the velocity information of the ultrasound beam direction for the bloodstream. As described in, for example, Patent Document 1 (JP 2013-192643 A), the velocity vector calculator 40 uses, in addition to the velocity information of the ultrasound beam direction for the bloodstream, motion information of a heart wall, to obtain the two-dimensional velocity vector of the bloodstream at each position in the scanning plane.

In forming the distribution of the two-dimensional velocity vector in the scanning plane using one-dimensional velocity information along the ultrasound beam direction, various known methods may be used. Alternatively, two ultrasound beams having different directions from each other may be formed, velocity information may be obtained from each of the two ultrasound beams, and the two-dimensional velocity vector may be formed therefrom.

The velocity vector calculator 40 obtains, for a plurality of sample points in a calculation coordinate system corresponding to a space to and from which the ultrasound is transmitted and received, a velocity vector for each sample point. For example, the calculation coordinate system is represented by an xyz orthogonal coordinate system, and a velocity vector is obtained for each sample point in an xy plane corresponding to the scanning plane of the ultrasound, to form a distribution of the two-dimensional velocity vector. Alternatively, as the scanning coordinate system corresponding to the scanning of the ultrasound, for example, an rθ coordinate system with a beam depth direction r and a beam scan direction θ may be employed, and the distribution of the two-dimensional velocity vector may be formed in the rθ coordinate system.

The velocity vector calculator 40 generates each vector frame showing the distribution of the two-dimensional velocity vectors formed from velocity vectors corresponding to a plurality of sample points (a plurality of coordinates). In addition, the velocity vector calculator 40 sequentially generates a plurality of vector frames over a plurality of time phases.

A region-of-interest setter 42 sets a region of interest corresponding to an inner cavity of the heart in the image data obtained by the process by the image former 20. The region-of-interest setter 42 sets, as the region of interest, a region surrounded by an inner cavity line which is set as an outer periphery of the inner cavity of the heart in the image data, a flow-in line which is set on a flow path of the bloodstream flowing into the inner cavity of the heart, and a flow-out line which is set on the flow path of the bloodstream flowing out from the inner cavity of the heart.

Figure 2:
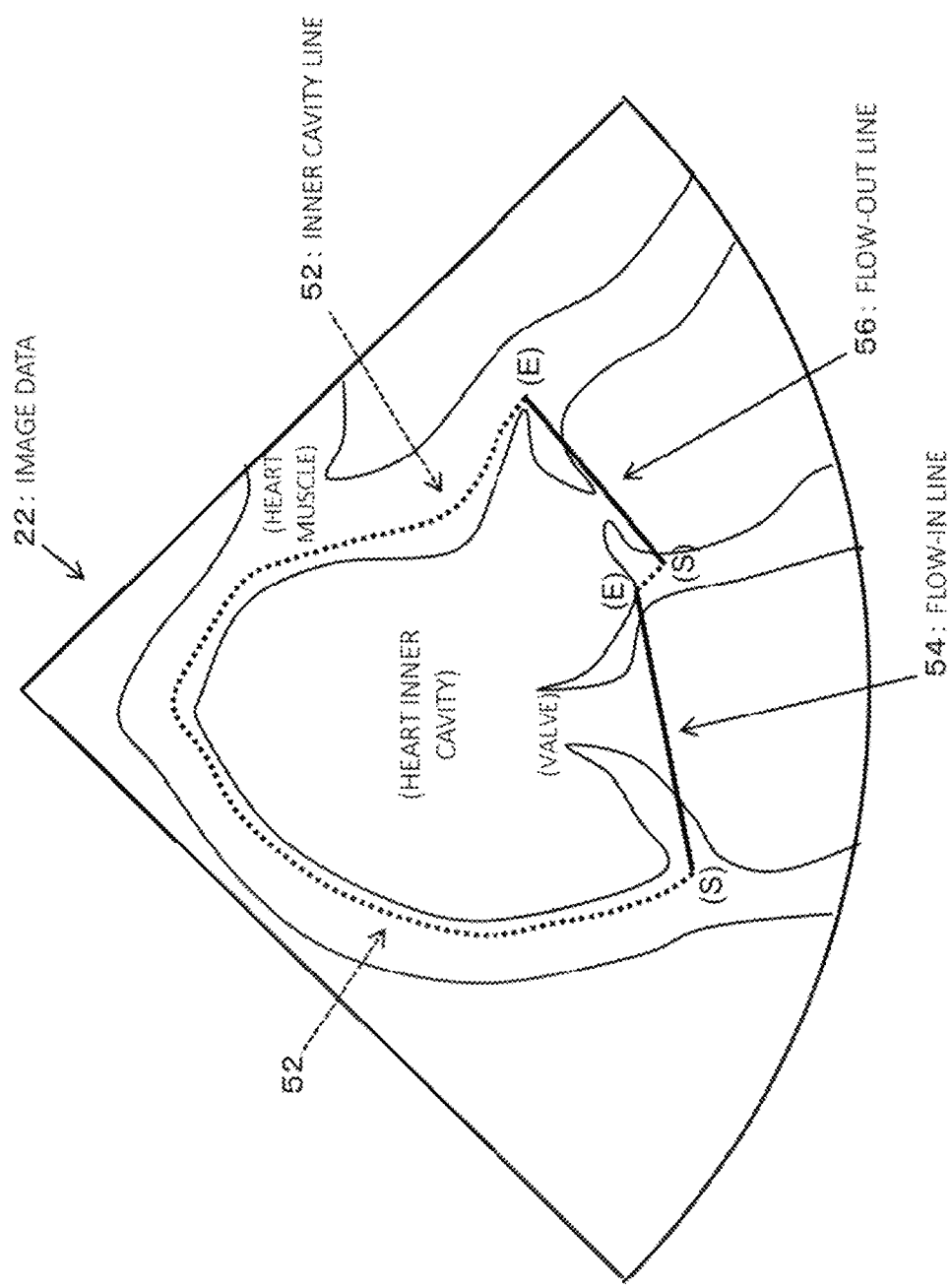
FIG. 2 is a diagram showing a specific example of a region of interest corresponding to an inner cavity of a heart.

FIG. 2 is a diagram showing a specific example of the region of interest corresponding to the inner cavity of the heart. FIG. 2 shows a specific example of image data 22 obtained by the image former 20. The image data 22 of FIG. 2 include the inner cavity of the heart surrounded at the periphery by a heart muscle and a valve.

The region-of-interest setter 42 sets, as the region-of-interest and in the image data 22, a region surrounded by an inner cavity line 52 which is set as an outer periphery of the inner cavity of the heart, a flow-in line 54 which is set on the flow path of the bloodstream flowing into the inner cavity of the heart, and a flow-out line 56 which is set on the flow path of the bloodstream flowing out from the inner cavity of the heart.

The inner cavity line 52 is formed based on a plurality of trace points corresponding to the outer periphery of the inner cavity of the heart. For example, a display image corresponding to the image data 22 is displayed on a display 82, and a user such as a doctor uses an operation device 90 while viewing the display image, and sets a few (may be several) trace reference points on or near a boundary between the inner cavity of the heart and the heart muscle. Based on the trace reference points which are set by the user, for example, a plurality of trace points are added between the trace reference points by an interpolation process or the like. The inner cavity line 52 is then formed based on a plurality of sample points including the few trace reference points and a plurality of the added trace points. For example, the inner cavity line 52 is formed to connect the plurality of sample points to each other. Alternatively, the boundary between the inner cavity of the heart and the heart muscle may be specified by an image process on the image data 22 such as binarization process, and the inner cavity line 52 may be formed along the boundary.

The flow-in line 54 and the flow-out line 56 are set according to an operation from the user. For example, the user such as the doctor designates positions of a starting point S and an end point E while viewing the display image corresponding to the image data 22, to set the flow-in line 54 and the flow-out line 56.

When the flow-in line 54 and the flow-out line 56 are initially set by the user, the region-of-interest setter 42 corrects the flow-in line 54 such that the inner cavity line 52 and the flow-in line 54 are connected to each other, corrects the flow-out line 56 such that the inner cavity line 52 and the flow-out line 56 are connected to each other, and connects the flow-in line 54 and the flow-out line 56.

For example, the region-of-interest setter 42 moves the starting point S of the flow-in line 54 to a position of a sample point (the trace point or the trace reference point) on the inner cavity line 52 closest to the starting point S. Further, the region-of-interest setter 42 moves the end point E of the flow-out line 56 to a position of a sample point (the trace point or the trace reference point) on the inner cavity line 52 closest to the end point E. In addition, the region-of-interest setter 42 forms a straight line or a curved line connecting the end point E of the flow-in line 54 and the starting point S of the flow-out line 56.

In this manner, the region-of-interest setter 42 forms a region surrounded by the inner cavity line 52, the flow-in line 54, and the flow-out line 56, and sets the region as the region of interest. FIG. 2 shows a specific example in which the flow-in line 54 and the flow-out line 56 are straight lines, but alternatively, lines other than straight lines may be employed.

Figure 3:
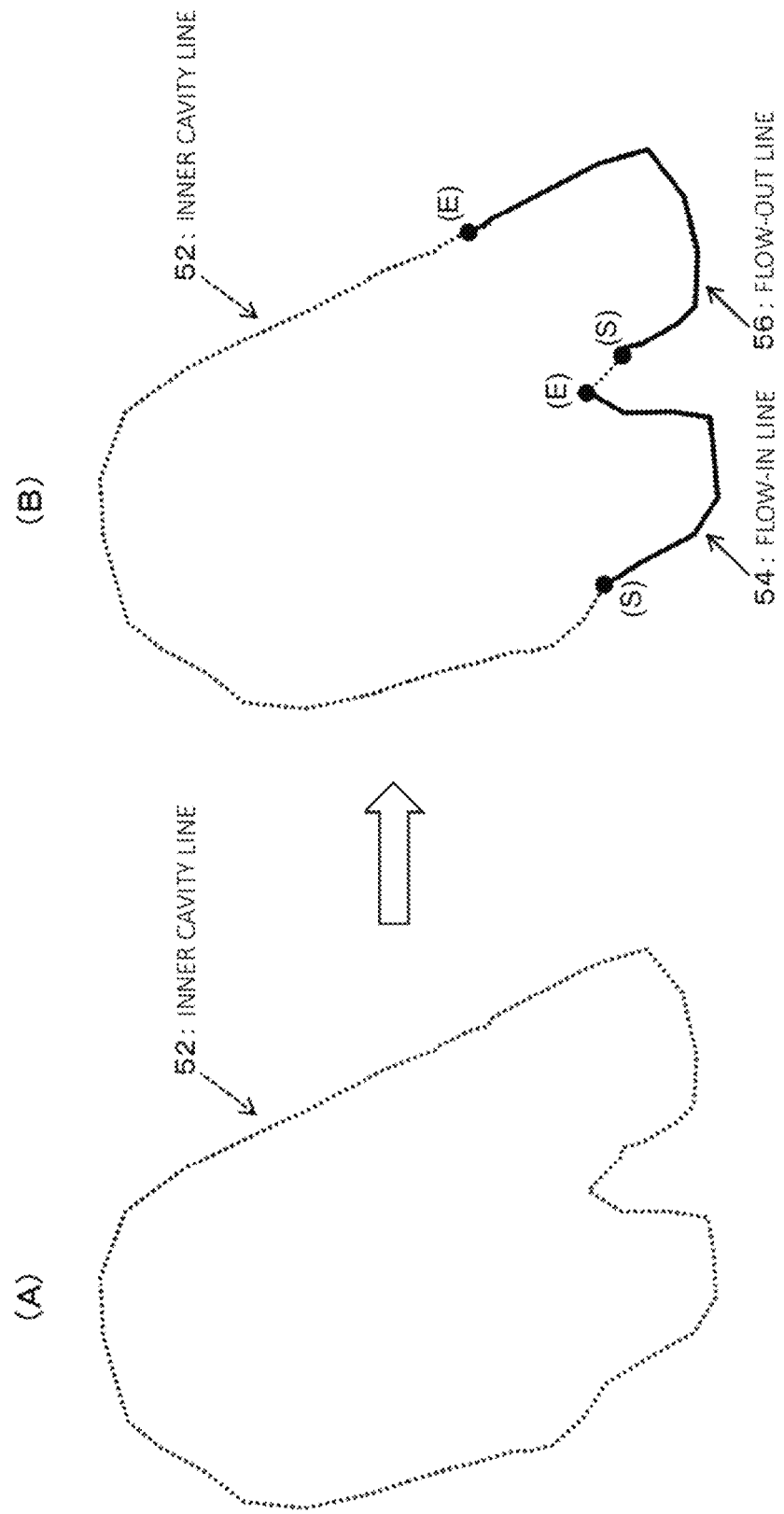
FIG. 3 is a diagram showing another specific example of a flow-in line and a flow-out line.

FIG. 3 is a diagram showing another specific example of the flow-in line 54 and the flow-out line 56. When, for example, the inner cavity line 52 of a closed curved line is obtained as in the specific example of FIG. 3(A), the flow-in line 54 and the flow-out line 56 in the form of a curved line connecting the starting point S and the end point E along the inner cavity line 52 may be formed, as shown in FIG. 3(B).

Referring again to FIG. 1, an inner cavity line velocity calculator 44 generates velocity information of the heart muscle (the heart wall) on the inner cavity line (reference numeral 52 in FIG. 2), based on the image data formed by the image former 20. The inner cavity line velocity calculator 44 generates velocity information of the heart muscle of each sample point, for the plurality of sample points on the inner cavity line.

The inner cavity line velocity calculator 44 tracks, for example, between frames of image data obtained over a plurality of frames, the movement position of the sample point in the two-dimensional plane over the plurality of frames for each sample point on the inner cavity line by a pattern matching using correlation calculation or the like based on pixel values (brightness values or the like) of the image data. With this process, for each sample point, two-dimensional movement information is obtained, and, for example, based on an amount of movement (movement vector) between the frames and the time between the frames, a two-dimensional velocity vector is calculated. When the image data are data corresponding to the xy orthogonal coordinate system, a velocity vector in the xy orthogonal coordinate system is calculated. Alternatively, when the image data are data corresponding to the rθ coordinate system, a velocity vector in the rθ coordinate system is calculated.

A result of tracking of each sample point on the inner cavity line by the inner cavity line velocity calculator 44 is also sent to the region-of-interest setter 42, and the region-of-interest setter 42 changes a shape of the inner cavity line so that the movements of the plurality of sample points are followed. Moreover, the region-of-interest setter 42 causes the starting point S and the end point E (refer to FIG. 2) to follow the movement of the sample points corresponding thereto. With this process, the flow-in line 54 and the flow-out line 56 are set according to the change of the shape of the inner cavity line; that is, following the motion of the heart in the image data.

When the two-dimensional velocity vector of the bloodstream is obtained in the velocity vector calculator 40 by the method of Patent Document 1, motion information of the heart wall is used. In this case, as the motion information of the heart wall, the velocity vector at each sample point on the inner cavity line calculated by the inner cavity line velocity calculator 44 is used.

Processes and functions of an interpolation processor 50, a particle generator 60, and a particle calculator 70 will be described later with reference to the drawings.

A display processor 80 forms a bloodstream display image based on the image data of the ultrasound image obtained from the image former 20 and a calculation result obtained from the particle calculator 70. The bloodstream display image formed by the display processor 80 is displayed on the display 82.

A controller 100 controls an overall operation in the ultrasound diagnostic apparatus of FIG. 1. In the overall control of the controller 100, instructions received from the user such as the doctor and the inspection technician through the operation device 90 are also reflected.

Of the structures shown in FIG. 1 (units assigned with reference numerals), the transmission and reception unit 12, the image former 20, the Doppler processor 30, the velocity vector calculator 40, the region-of-interest setter 42, the inner cavity line velocity calculator 44, the interpolation processor 50, the particle generator 60, the particle calculator 70, and the display processor 80 may be realized, for example, using hardware such as an electric/electronic circuit and a processor, and a device such as a memory may be used as necessary, in the realization of these units. Alternatively, at least a part of the functions corresponding to the above-described units may be realized by a computer. In other words, at least a part of the functions corresponding to the above-described units may be realized by cooperation between hardware such as a CPU, a processor, and a memory, and software (program) defining operations of the CPU and the processor.

A desirable specific example of the display 82 is a liquid crystal display, and the operation device 90 may be realized by, for example, at least one of a mouse, a keyboard, a trackball, a touch panel, and other switches. The controller 100 may be realized, for example, by cooperation between the hardware such as the CPU, the processor, and the memory, and software (program) defining operations of the CPU and the processor.

The overall structure of the ultrasound diagnostic apparatus of FIG. 1 has been described. Next, specific examples of the functions realized by the ultrasound diagnostic apparatus of FIG. 1 will be described in detail. The structures (units assigned with reference numerals) shown in FIG. 1 are described in the following with reference numerals assigned in FIG. 1.

Figure 4:
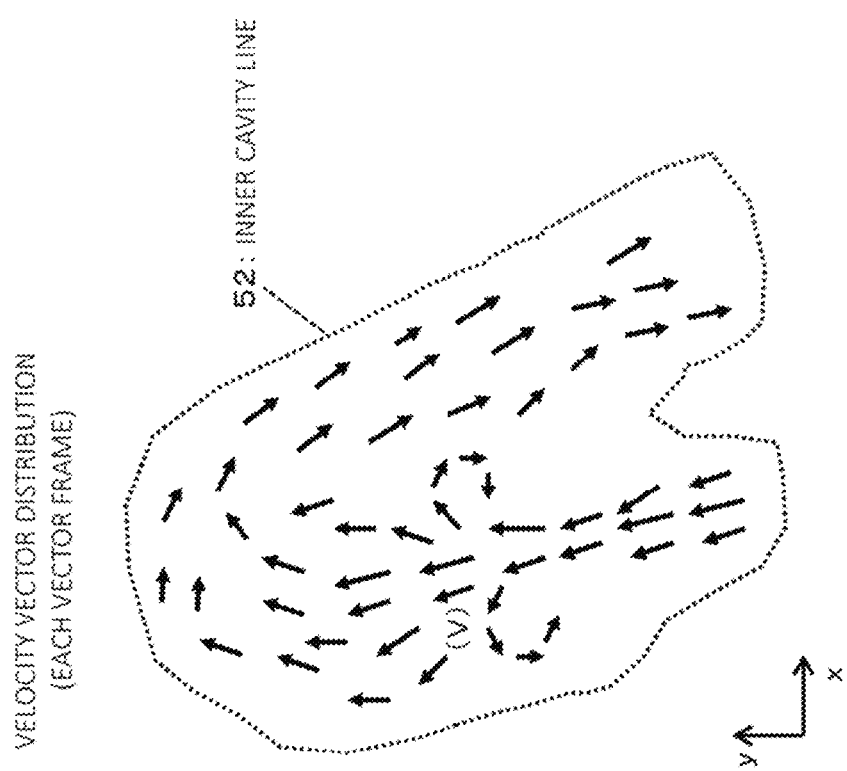
FIG. 4 is a diagram showing a specific example of a velocity vector distribution.

FIG. 4 is a diagram showing a specific example distribution of velocity vectors. The velocity vector calculator 40 uses velocity information of the ultrasound beam direction for the bloodstream and the motion information of the heart wall, as described in, for example, Patent Document 1 (JP 2013-192643 A), to obtain a two-dimensional velocity vector of the bloodstream at each position in the scanning plane. More specifically, a velocity vector distribution, for example, as shown in FIG. 4, is formed based on the velocity information of the ultrasound beam direction obtained from the Doppler processor 30 (Doppler information), and the velocity information at each sample point on the inner cavity line 52 obtained from the inner cavity line velocity calculator 44.

The velocity vector distribution shown in FIG. 4 is represented in the xy coordinate system (orthogonal coordinate system) including the inner cavity line 52 of the heart (refer to FIG. 2), and is formed from a plurality of velocity vectors (velocity vectors of the bloodstream) V calculated at a plurality of coordinates in the xy coordinate system. The velocity vector calculator 40, for example, first forms a two-dimensional velocity vector distribution in a scanning coordinate system corresponding to the scanning of the ultrasound, for example, in the rθ coordinate system with the beam depth direction r and the beam scan direction θ, and then applies a coordinate conversion process to obtain the velocity vector distribution of the xy coordinate system as shown in FIG. 4.

The velocity vector calculator 40 generates each vector frame formed from velocity vectors V corresponding to a plurality of sample points (a plurality of coordinates); that is, each vector frame showing the two-dimensional vector distribution. The velocity vector calculator 40 sequentially generates a plurality of vector frames over a plurality of time phases. In this manner, a vector frame array comprising a plurality of vector frames is obtained.

Figure 5:
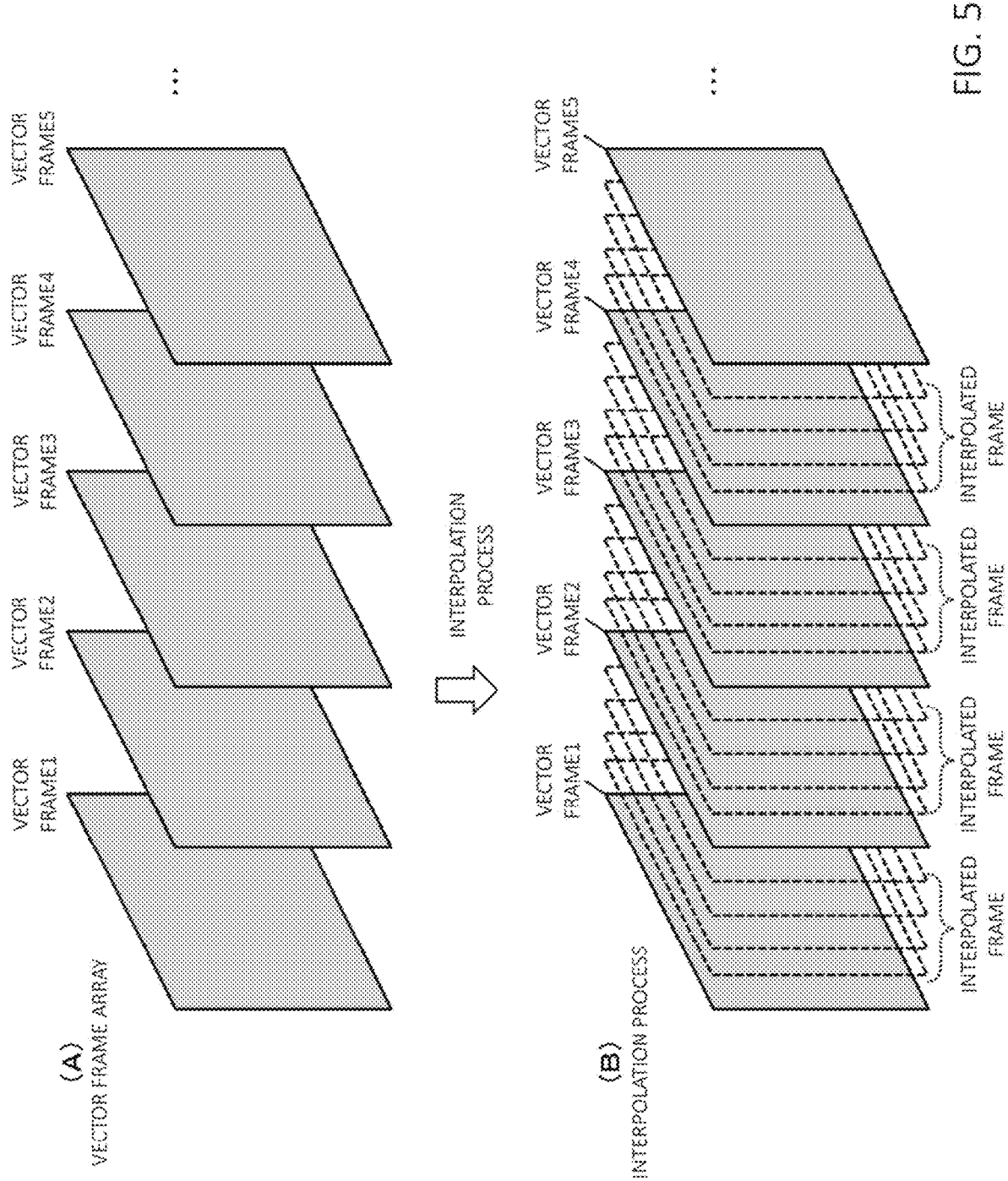
FIG. 5 is a diagram for explaining a frame array.

FIG. 5 is a diagram for explaining the frame array. FIG. 5(A) shows a specific example of the vector frame array. In the specific example of FIG. 5(A), the vector frame array is formed from a plurality of vector frames (1~5 are shown as representative frames).

Each vector frame formed from the velocity vectors at the plurality of coordinates is generated using the velocity information of the ultrasound beam direction (Doppler information) obtained from the Doppler processor 30. In obtaining the Doppler information, for example, if the transmission and reception of color Doppler method is used, because the ultrasound is repeatedly transmitted and received in the same beam direction, the transmission and reception frame rates when the Doppler information is obtained are lower as compared to a case where, for example, the B-mode image is obtained. Because the velocity vectors of each vector frame are calculated using the Doppler information, the frame rate of the vector frame array would also be relatively low.

In consideration of this, the interpolation processor 50 executes an inter-frame interpolation process for the vector frame array. FIG. 5(B) shows a specific example of an interpolated frame array to which the inter-frame interpolation process is applied. In the specific example shown in FIG. 5(B), the interpolated frame array comprises the plurality of vector frames (1~5 shown in FIG. 5(A) as representative frames), and a plurality of interpolated frames added between the vector frames. Each interpolated frame is generated by applying the interpolation process based on the velocity vector between two vector frames which are adjacent to each other.

Alternatively, a frame rate of the interpolated frame array may be determined based on, for example, a display frame rate at the display 82. More specifically, when, for example, the display frame rate is 60 Hz, the number of interpolated frames to be added, or the like is determined such that the frame rate of the interpolated frame array is also 60 Hz. Needless to say, it is not always necessary to match the display frame rate and the frame rate of the interpolated frame array.

Figure 6:
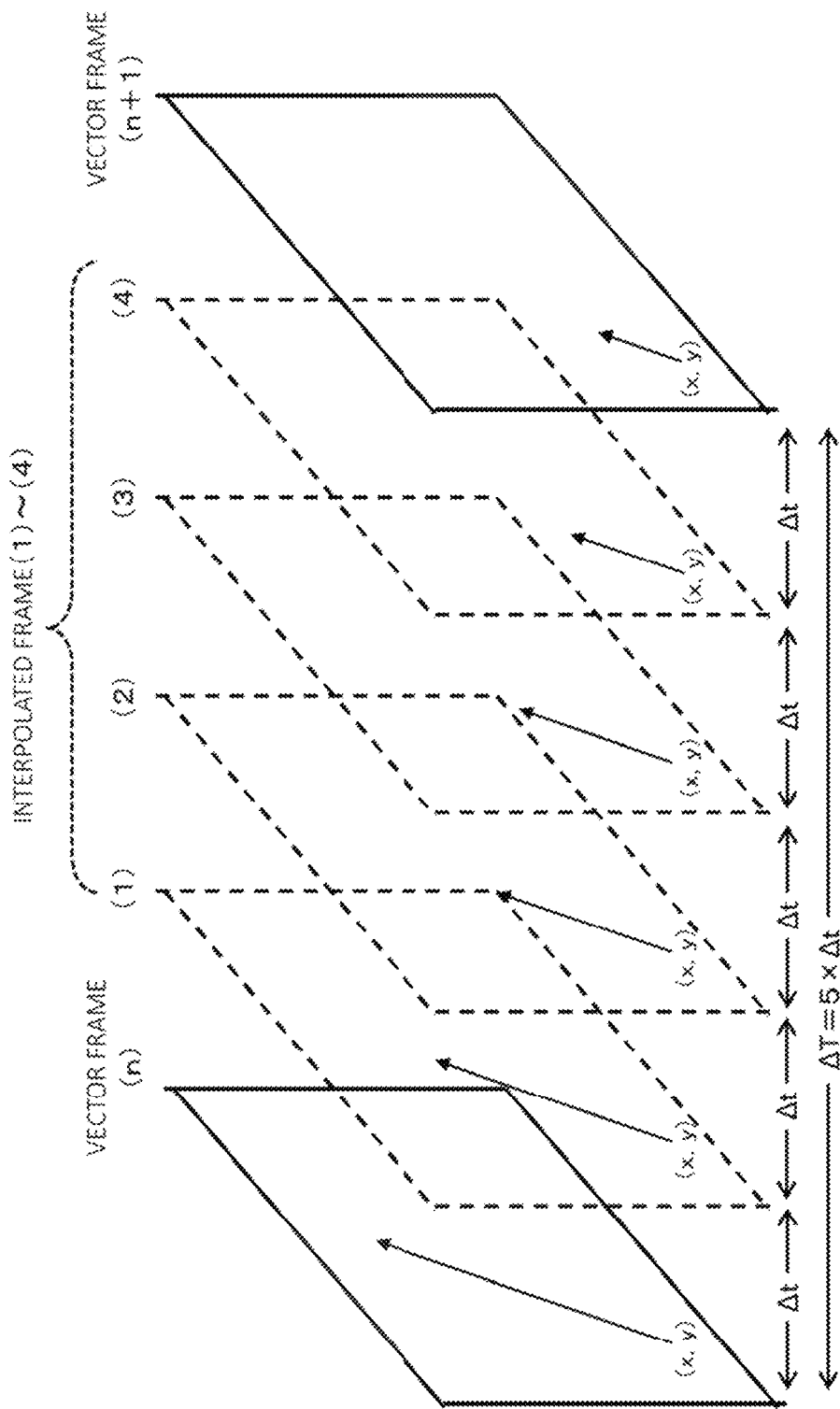
FIG. 6 is a diagram for explaining an interpolation process between frames.

FIG. 6 is a diagram for explaining the interpolation process between the frames. The interpolation processor 50 applies the interpolation process between two vector frames which are adjacent to each other in the vector frame array formed from a plurality of vector frames (refer to FIG. 5), and adds one or a plurality of interpolated frames between the vector frames. Each interpolated frame is formed from interpolated vectors at a plurality of coordinates.

The interpolation processor 50 applies, for each coordinate, an interpolation process based on two velocity vectors corresponding to the coordinate obtained from two vector frames which are adjacent to each other, to calculate the interpolated vector corresponding to the coordinate.

FIG. 6 shows a specific example of the inter-frame interpolation process at a coordinate (x, y). In FIG. 6, a vector frame (n) and a vector frame (n+1) are two vector frames which are adjacent to each other in the vector frame array. In the specific example of FIG. 6, 4 interpolated frames (1)~(4) are added at equal intervals between the vector frame (n) and the vector frame (n+1). A time interval between the vector frame (n) and the vector frame (n+1) is ΔT, and 4 interpolated frames (1)~(4) are added with an equal interval Δt within ΔT. Thus, ΔT=5×Δt.

The interpolation processor 50 calculates the interpolated vectors forming each interpolated frame by, for example, linear interpolation corresponding to the time interval. For example, when the velocity vector (x-direction component, y-direction component) at the coordinate (x, y) in the vector frame (n) is (Vx0, Vy0), and the velocity vector (x-direction component, y-direction component) at the coordinate (x, y) in the vector frame (n+1) is (Vx1, Vy1), the x-direction component and the y-direction component of the interpolated vector at each coordinate (x, y) in the interpolated frames (1)~(4) are calculated by the following Equations 1 to 4.

(Equation 1)
Interpolated vector at the coordinate (x, y) in the interpolated frame (1):

$$x\text{-direction component}=\{(Vx0\cdot 4\Delta t)+(Vx1\cdot \Delta t)\}/5\Delta t$$

$$y\text{-direction component}=\{(Vy0\cdot 4\Delta t)+(Vy1\cdot \Delta t)\}/5\Delta t$$

(Equation 2)
Interpolated vector at the coordinate (x, y) in the interpolated frame (2):

$$x\text{-direction component}=\{(Vx0\cdot 3\Delta t)+(Vx1\cdot 2\Delta t)\}/5\Delta t$$

$$y\text{-direction component}=\{(Vy0\cdot 3\Delta t)+(Vy1\cdot 2\Delta t)\}/5\Delta t$$

(Equation 3)
Interpolated vector at the coordinate (x, y) in the interpolated frame (3):

$$x\text{-direction component}=\{(Vx0\cdot 2\Delta t)+(Vx1\cdot 3\Delta t)\}/5\Delta t$$

$$y\text{-direction component}=\{(Vy0\cdot 2\Delta t)+(Vy1\cdot 3\Delta t)\}/5\Delta t$$

(Equation 4)
Interpolated vector at the coordinate (x, y) in the interpolated frame (4):

$$x\text{-direction component}=\{(Vx0\cdot \Delta t)+(Vx1\cdot 4\Delta t)\}/5\Delta t$$

$$y\text{-direction component}=\{(Vy0\cdot \Delta t)+(Vy1\cdot 4\Delta t)\}/5\Delta t$$

The above-described Equations 1 to 4 are merely one specific example when linear interpolation according to the time interval is used, and alternatively, linear interpolation may be realized using other equations. Alternatively, the interpolated vector may be calculated using an interpolation process other than linear interpolation. Further, when the interpolated vector is calculated at each coordinate, reference may be made to velocity vectors of other coordinates, for example, a nearby coordinate. In addition, for example, in the interpolation process between the vector frame (n) and the vector frame (n+1), there may be used a velocity vector in a vector frame other than the two vector frames, for example, a vector frame near the two vector frames.

The interpolation processor 50 obtains, for the plurality of coordinates for which the velocity vector distribution is obtained, the interpolated vectors by executing the interframe interpolation process for each coordinate, to form each interpolated frame formed from the interpolated vectors at the plurality of coordinates. In this manner, the interpolated frame array (refer to FIG. 5(B)), formed from the plurality of vector frames and the plurality of interpolated frames added between the vector frames, is obtained. Based on the interpolated frame array, movement destinations of the plurality of virtual particles related to the bloodstream are calculated. The plurality of virtual particles are generated by the particle generator 60.

Figure 7:
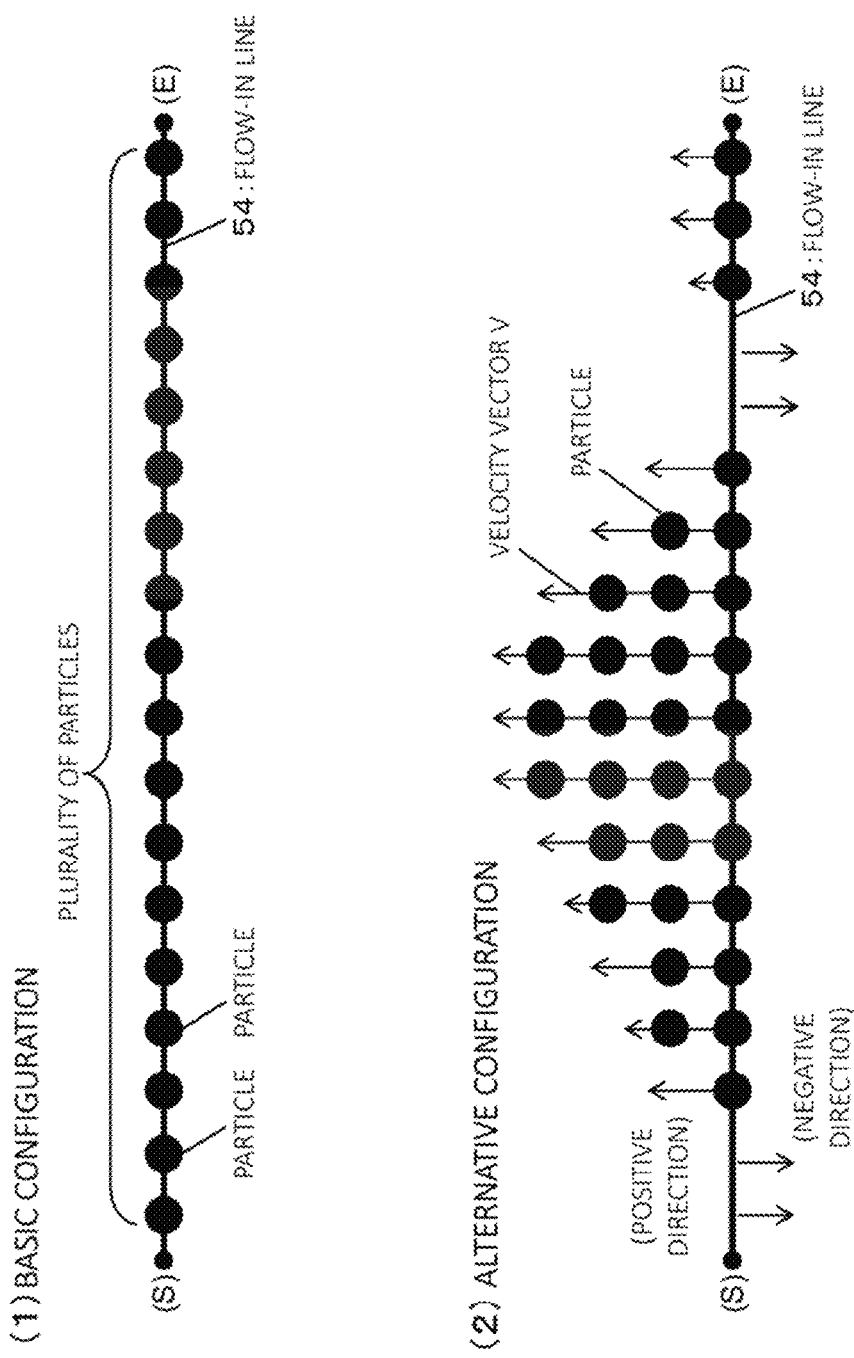
FIG. 7 is a diagram for explaining generation of a plurality of particles.

FIG. 7 is a diagram for explaining the generation of the plurality of particles. The particle generator 60 sets the plurality of particles related to the bloodstream in the coordinate system including the bloodstream; that is, the coordinate system in the ultrasound image and in which the two-dimensional velocity vector distribution is formed. The particle generator 60 generates the plurality of particles on the flow-in line 54 which is set with respect to the heart in the ultrasound image, for example. In this case, the flow-in line 54 is set as a generation line on which the plurality of particles are generated.

As shown as a basic configuration (1) in FIG. 7, for example, on the flow-in line 54 connecting the starting point S and the end point E by a straight line, the plurality of particles arranged in a line are generated with equal spacing therebetween. For example, 50 particles are generated with equal spacing on the flow-in line 54. When a length of the flow-in line 54 is less than or equal to 50 pixels, one particle is generated for each pixel on the flow-in line 54. Alternatively, the plurality of particles may be generated in a set number other than 50. Alternatively, the user may set or change the number for the plurality of particles.

The particle generator 60 may generate the plurality of particles for only particular frame (only one time phase), but desirably, the particle generator 60 generates the plurality of particles periodically in each frame over a plurality of frames. For example, the plurality of particles may be generated for each vector frame in the vector frame array formed from a plurality of vector frames (FIG. 5(A)), or the plurality of particles may be generated in each vector frame and each interpolated frame in the interpolated frame array (FIG. 5(B)). Alternatively, the plurality of particles may be generated in the frames with a few frame interval therebetween.

If the flow-in line 54 is set by the region-of-interest setter 42 to follow the motion of the heart in the image data of the ultrasound image, the plurality of particles can be generated while correcting the positions so that the motion of the heart is followed.

In addition, as shown in FIG. 7 as an alternative configuration (2), the generation form of the plurality of particles may be varied depending on a magnitude and a direction of the velocity vector V on the flow-in line 54. In the alternative configuration (2), as the magnitude of the velocity vector V (for example, a vertical component with respect to the flow-in line 54) becomes larger, the number of particles at the position of the velocity vector V is increased. In addition, in the alternative configuration (2), the particles are generated at the position of the velocity vector V only when the velocity vector V is in a positive direction. Alternatively, the direction for generating the particles (positive or negative) may be set, for example, by the user.

The particle generation is not limited to the specific examples shown in FIG. 7, and, for example, the particle generator 60 may generate the plurality of particles on the flow-in line 54 having a curved line shape (refer to FIG. 3). Further, the particle generation is not limited to generation on the flow-in line 54, and, for example, the plurality of particles may be generated on a generation line or in a generation region designated by the user, or the plurality of particles may be generated, for example, two-dimensionally uniformly (for example, in a lattice shape) in the region of interest which is set by the region-of-interest setter 42.

When the plurality of particles are generated by the particle generator 60, the particle calculator 70 calculates the movement destination of the particle for each of the particles, based on the interpolated frame array (FIG. 5(B)).

Figure 8:
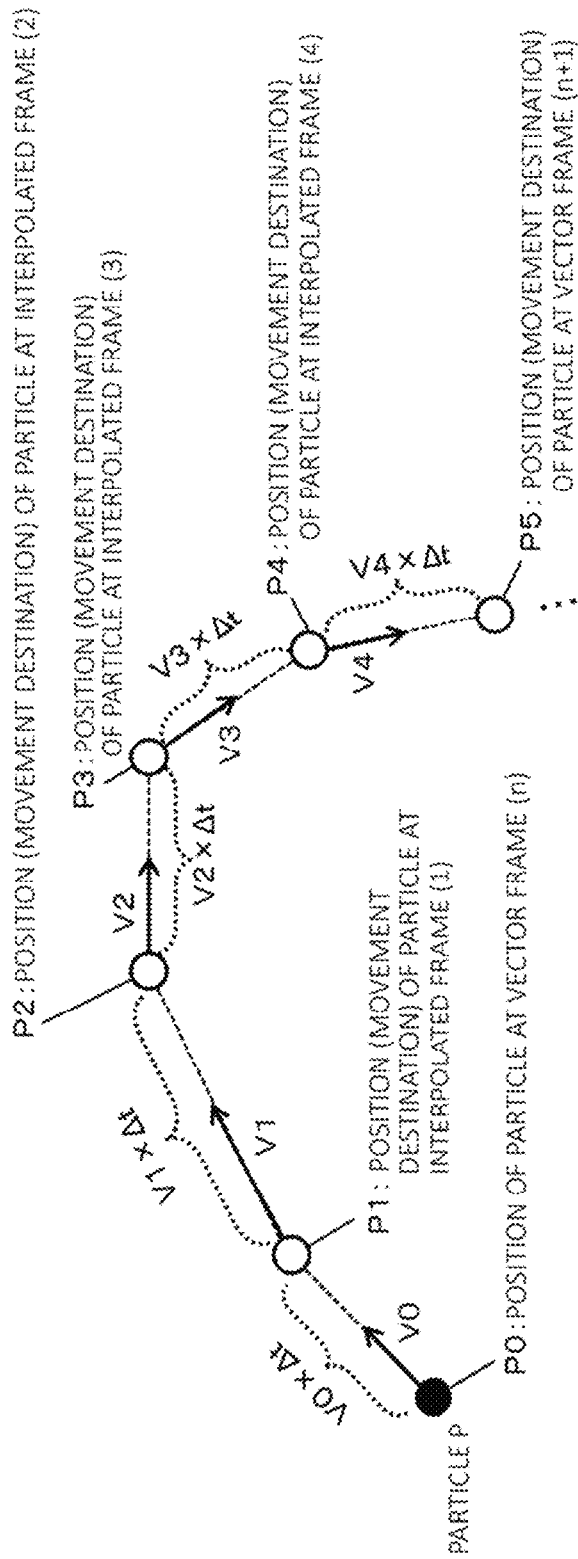
FIG. 8 is a diagram for explaining a specific example calculation of a movement destination of each particle.

FIG. 8 is a diagram for explaining a specific example of calculation of the movement destination of each particle. FIG. 8 shows a specific example calculation related to one particle P based on the interpolated frame array (refer to FIG. 6) in which 4 interpolated frames (1)~(4) are added at equal intervals between the vector frame (n) and the vector frame (n+1).

When the particle P exists at a position P0 (coordinate P0) in the vector frame (n), for example, when the particle P is generated at the position P0 in the vector frame (n), first, a velocity vector V0 of the bloodstream at the position P0 is used. If there is a velocity vector of a coordinate corresponding to the position P0 (coordinate P0) in the velocity vectors of the plurality of coordinates of the vector frame (n), this velocity vector is set as the velocity vector V0. If there is no velocity vector of the coordinate corresponding to the position P0, the velocity vector V0 is calculated by a linear interpolation process (in-frame interpolation process) or the like based on the velocity vectors of the plurality of coordinates in proximity to the position P0.

The velocity vector V0 is multiplied with the frame interval $\Delta t$ (refer to FIG. 6), to calculate the movement vector (having a magnitude of $\Delta t$ times that of the velocity vector V0 and the same direction as the velocity vector V0), and a position P1 (coordinate P1), which is a position moved from the position P0 by the movement vector, is calculated. The position P1 thus obtained is the position of the particle P (movement destination coordinate) in the interpolated frame (1) which is a next frame (next time phase) of the vector frame (n).

Next, a velocity vector V1 of the bloodstream at the position P1 is used. If there is an interpolated vector of the coordinate corresponding to the position P1 (coordinate P1) in the interpolated vectors of the plurality of coordinates of the interpolated frame (1), this interpolated vector is set as the velocity vector V1. If there is no interpolated vector of the coordinate corresponding to the position P1, the velocity vector V1 is calculated by the linear interpolation process (in-frame interpolation process) or the like based on the interpolated vectors of the plurality of coordinates in proximity to the position P1.

The velocity vector V1 is then multiplied with the frame interval $\Delta t$, to calculate the movement vector (having a magnitude which is $\Delta t$ times that of the velocity vector V1 and the same direction as the velocity vector V1), and a position P2 (coordinate P2), which is a position moved from the position P1 by the movement vector, is derived. The position P2 thus obtained is the position of the particle P (movement destination coordinate) in the interpolated frame (2) which is a next frame (next time phase) of the interpolated frame (1).

In the interpolated frame (3) and the interpolated frame (4) following the interpolated frame (2), processes similar to those described above are executed. Thus, the movement destination coordinate of the particle P is calculated based on the movement vector obtained by multiplying the velocity vector (V2, V3) at the position of the particle P with the frame interval $\Delta t$. In the specific example of FIG. 8, the position P3 in the interpolated frame (3) and the position P4 in the interpolated frame (4) are the movement destination coordinates of the particle P.

Further, a velocity vector V4 of the bloodstream at the position P4 is used. If there is an interpolated vector of a coordinate corresponding to the position P4 (coordinate P4) in the interpolated vectors of the plurality of coordinates of the interpolated frame (4), this interpolated vector is set as the velocity vector V4. If there is no interpolated vector of the coordinate corresponding to the position P4, the velocity vector V4 is calculated by the linear interpolation process (in-frame interpolation process) or the like based on the interpolated vectors of the plurality of coordinates in proximity to the position P4.

The velocity vector V4 is multiplied by the frame interval $\Delta t$ to calculate the movement vector (having a magnitude which is $\Delta t$ times that of the velocity vector V4 and the same direction as the velocity vector V4), and a position P5 (coordinate P5), which is a position moved from the position P4 by the movement vector, is derived. The position P5 thus obtained is the position of the particle P (movement destination coordinate) in the vector frame (n+1) which is a next frame (next time phase) of the interpolated frame (5).

In this manner, the particle calculator 70 executes processes similar to those described above in the plurality of frames (interpolated frames or vector frames) subsequent to the vector frame (n+1), to sequentially derive the movement destination of the particle P until a completion condition to be described later is satisfied. The particle calculator 70 derives, for each of the plurality of particles generated by the particle generator 60, the movement destination of the particle from the frame (time phase) in which the particle is generated.

According to the specific example of FIG. 8, the movement destination of each particle is derived based on the interpolated frame array in which the plurality of interpolated frames are added between the vector frames, and thus, an estimation precision of the movement destination can be improved as compared to the case where the plurality of interpolated frames are not added.

For example, if the interpolated frames (1)~(4) in FIG. 8 are not used, and a position moved from the position P0 of the particle P in the vector frame (n) by a movement vector obtained by multiplying the velocity vector V0 with the vector frame interval $\Delta T$ (refer to FIG. 6) (having a magnitude which is $\Delta T$ times that of the velocity vector V0 and the same direction as the velocity vector V0) is set as the movement destination of the particle P in the vector frame (n+1), a movement destination completely different from the position P5 (coordinate P5) obtained in the specific example of FIG. 8 would be obtained. This is because, when the interpolated frames (1)~(4) are not used, the change of the velocity vector of the particle P between the vector frame (n) and the vector frame (n+1) is not reflected.

Figure 9:
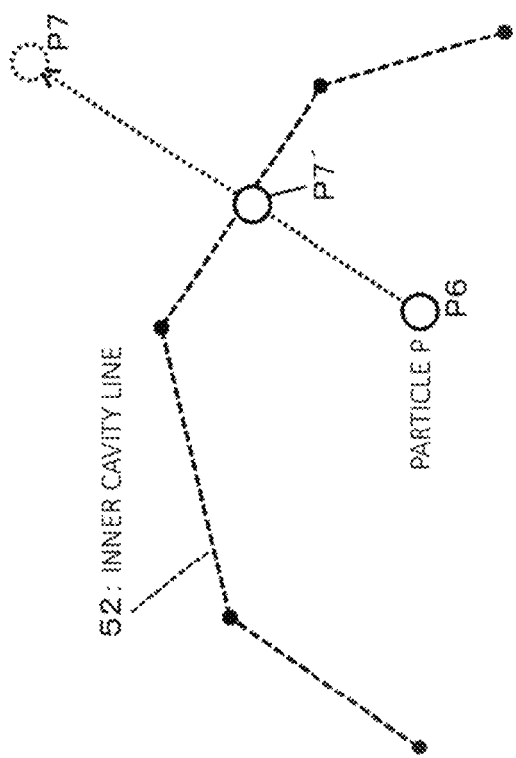
FIG. 9 is a diagram for explaining an exception process of calculation of a movement destination of each particle.

FIG. 9 is a diagram for explaining an exception process of calculation of the movement destination of each particle. The particle calculator 70 derives the movement destination of each particle by the basic process explained with reference to FIG. 8, but when the movement destination of each particle goes beyond the inner cavity line 52 as shown in FIG. 9, the movement destination of each particle is corrected to a position on the inner cavity line 52 or near the inner cavity line 52 and at the inner side (side of the heart cavity) of the inner cavity line 52.

For example, as shown in the specific example of FIG. 9, when the particle P is at a position P6 in each frame (vector frame or interpolated frame), and the movement destination at the next frame (vector frame or interpolated frame) obtained by the basic process is a position P7; that is, when the movement vector (an arrow with a broken line) crosses the inner cavity line 52, the movement destination in the next frame is corrected from the position P7 to a position P7'. In the specific example of FIG. 9, the position P7' is a crossing point between the inner cavity line 52 and the movement vector. Alternatively, a position near the crossing point, for example, a position near the crossing point and at an inner side (side of the heart cavity) of the inner cavity line 52, may be set as the position P7'.

Figure 10:
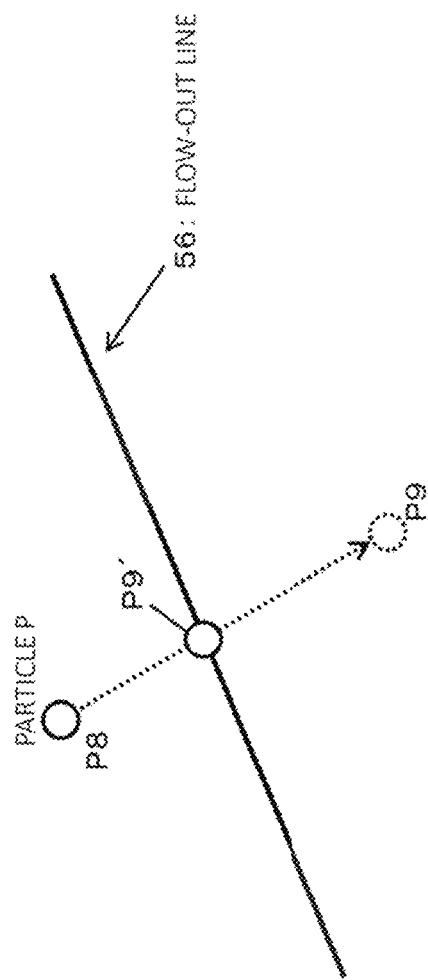
FIG. 10 is a diagram for explaining a completion condition of calculation of a movement destination of each particle.

FIG. 10 is a diagram for explaining a completion condition of the calculation of the movement destination of each particle. The particle calculator 70 sequentially derives the movement destination of each particle by the basic process explained above with reference to FIG. 8 and the exception process explained above with reference to FIG. 9, and completes the calculation of the movement destination of the particle when the movement destination of each particle passes the flow-out line 56, as shown in FIG. 10.

For example, as shown in the specific example of FIG. 10, when the particle P is at a position P8 in each frame (vector frame or interpolated frame), and the movement destination in the next frame (vector frame or interpolated frame) is a position P9; that is, when the movement vector (an arrow with a broken line) crosses the flow-out line 56, the particle calculator 70 corrects the movement destination in the next frame from the position P9 to a position P9', and completes the calculation of the movement destination of the particle P.

In the specific example of FIG. 10, the position P9' is a crossing point between the flow-out line 56 and the movement vector. Alternatively, a position near the crossing point, for example, a position near the crossing point and at an upper side (side of the heart cavity) of the flow-out line 56, may be set as the position P9'.

When the plurality of particles are generated by the particle generator 60 and the movement destination is sequentially calculated over a plurality of time phases (a plurality of frames) of the particle for each particle by the particle calculator 70, the display processor 70 forms a bloodstream display image in which a coordinate of the movement destination of each particle over the plurality of time phases is shown in the image. The display processor 80 forms, for example, an image of a path line in which the coordinate of the movement destination of each particle over the plurality of time phases is shown by a trajectory by at least one of a point and a line.

Figure 11:
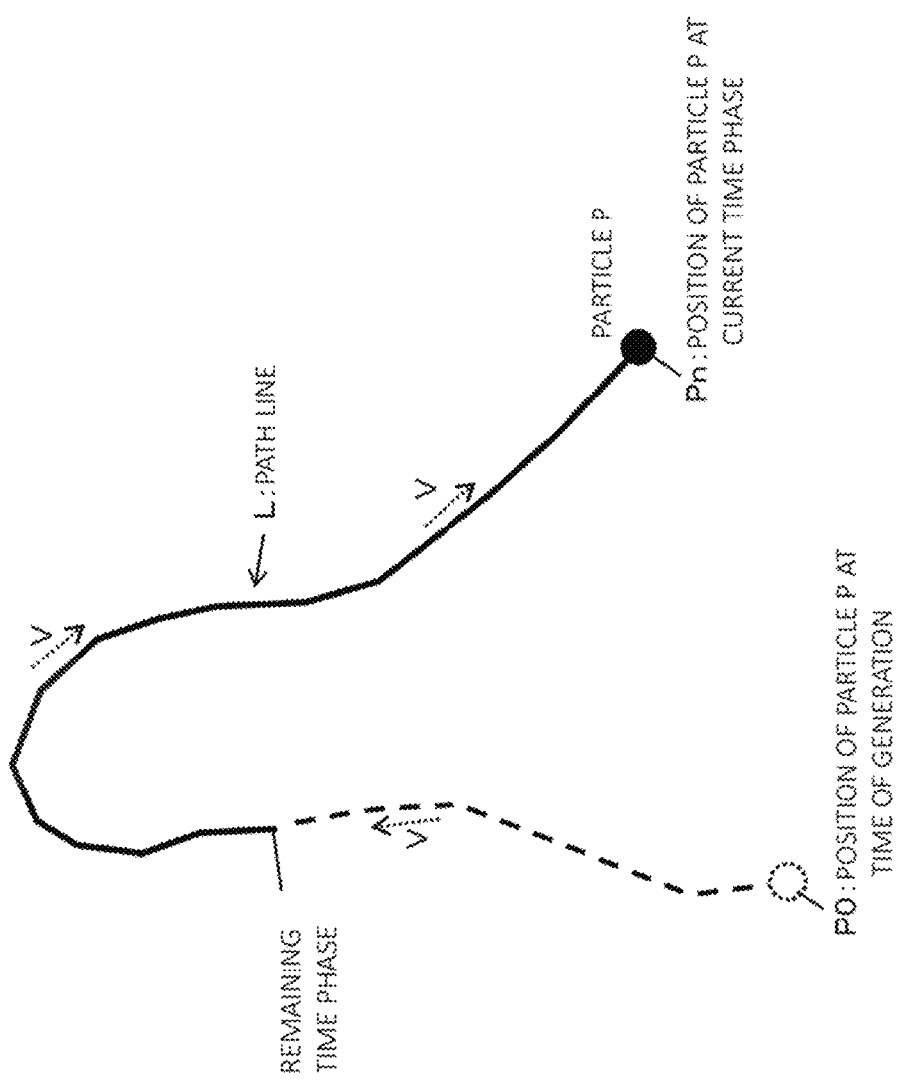
FIG. 11 is a diagram showing a specific example of a path line.

FIG. 11 is a diagram showing a specific example of the path line. FIG. 11 shows a path line L related to a particle P which is one of the plurality of particles. The path line L is a trajectory of the movement destinations of the particle P (plurality of positions corresponding to the plurality of time phases) sequentially calculated over the plurality of time phases (plurality of frames) in the interpolated frame array (FIG. 5(B) and FIG. 6). For example, the path line L is formed by connecting the movement destinations of the particle P over the plurality of time phases (for example, positions P0, P1, P2, P3, P4, P5, . . . in FIG. 8) by a straight line or a curved line (for example, a curved line based on spline interpolation) in the order to the time phases. Alternatively, on the path line L or in place of the path line L, the movement destinations of the particle P over the plurality of time phases (for example, positions P0, P1, P2, P3, P4, P5, . . . in FIG. 8) may be displayed by an array of a plurality of points.

Desirably, a length of the path line L to be displayed is suitably adjusted. For example, the display processor 80 forms the path line L from the time phase (current time phase) in which the trajectory of each particle is displayed to a time phase a predetermined time in the past of the current time phase (remaining time phase). In other words, as shown in the specific example of FIG. 11, as the path line L of the particle P, only a portion (solid line portion) of the path line L from the position Pn of the particle P at the current time phase to the remaining time phase which is a predetermined time prior to the current time phase is displayed, and the portion (broken line portion) of the path line L formed prior to the remaining time phase is not displayed. Further, it is desirable to employ a configuration such that the user can set the predetermined time period. For example, a configuration may be employed in which, by the user operating a key of the operation device 90, the user can determine the predetermined time period in a settable range of 100 ms~1000 ms, in units of 100 ms.

Alternatively, the display processor 80 may only display, for example, the portion of the path line L from the time phase where each particle is generated to a time phase which is a predetermined time thereafter.

Figure 12:
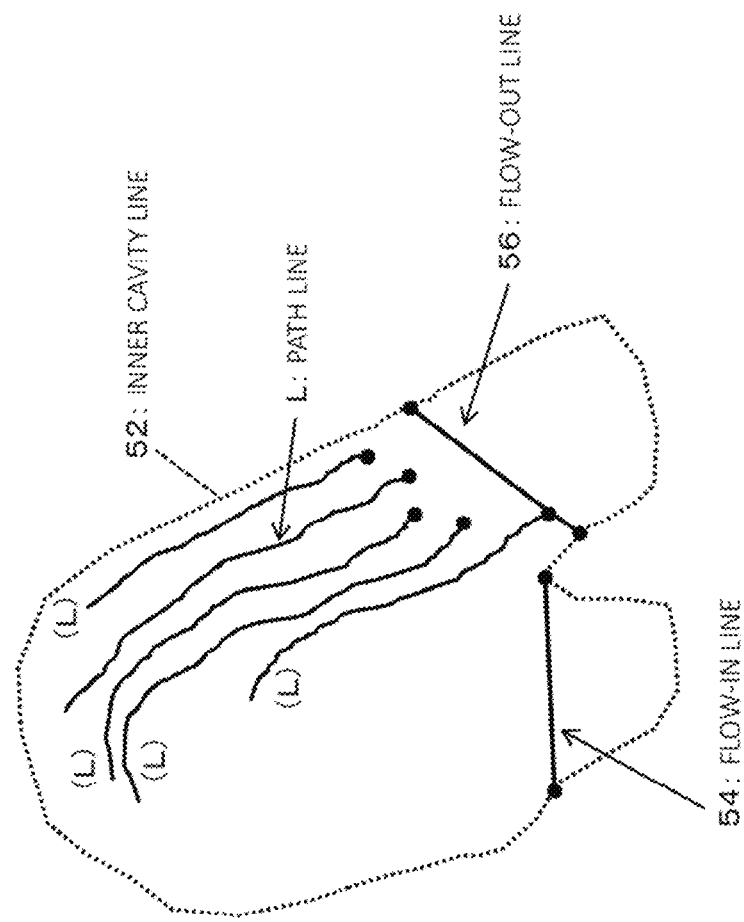
FIG. 12 is a diagram showing a specific example of a bloodstream display image.

FIG. 12 is a diagram showing a specific example of a bloodstream display image. The display processor 80 forms the path line L for each particle of the plurality of particles, and forms a bloodstream display image in which the path lines L of the plurality of particles are shown on the ultrasound image of the heart obtained from the image former 20. Alternatively, a bloodstream display image may be formed in which the path lines L of the plurality of particles are shown on the color Doppler image formed using the Doppler information obtained from the Doppler processor 30. The bloodstream display image formed by the display processor 80 is displayed on the display 82.

Alternatively, in place of displaying all of the plurality of path lines L corresponding to all of the generated particles, the number of path lines L to be displayed may be thinned. For example, a configuration may be employed in which, of many path lines L which are formed, only one line out of 10 lines may be displayed, to form an easy-to-view image by resolving crowding of many path lines L in the bloodstream display image. Further, for example, a configuration may be employed in which, by the user operating a key of the operation device 90, the user can set the number of path lines L to be displayed or the ratio of thinning.

The display processor 80 forms the bloodstream display image for each display time phase over the plurality of time phases. For example, the bloodstream display image (FIG. 12) corresponding to the display time phase is formed on the ultrasound image or the color Doppler image of the heart corresponding to each display time phase. With such a configuration, it becomes possible to visually and dynamically check a change of the path lines L of the plurality of particles over the plurality of time phases while checking, on the ultrasound image or the color Doppler image, the motion of the heart which dynamically changes over the plurality of time phases. Alternatively, a static image (freeze image) at a particular heartbeat time phase (such as, for example, telediastolic and telesystolic) desired by the user may be displayed. With such a configuration, for example, it becomes possible to visually and intuitively check the state of the bloodstream in the heart such as eddy flow, turbulent flow, and the stationary state.

An embodiment of the present disclosure has been described. The above-described embodiment, however, is merely exemplary in every aspect, and does not limit the scope of the present disclosure. The present disclosure includes various modifications within the scope not deviating from the principle thereof.

REFERENCE SIGNS LIST

10 PROBE; 12 TRANSMISSION AND RECEPTION UNIT; 20 IMAGE FORMER; 30 DOPPLER PROCESSOR;

40 VELOCITY VECTOR CALCULATOR; 50 INTERPOLATION PROCESSOR; 60 PARTICLE GENERATOR; 70 PARTICLE CALCULATOR; 80 DISPLAY PROCESSOR; 100 CONTROLLER.

The invention claimed is:

1. An ultrasound diagnostic apparatus comprising:
a vector calculator that obtains a bloodstream vector at each coordinate in a coordinate system including a bloodstream based on a signal obtained by transmitting and receiving ultrasound, to generate a plurality of vector frames formed from each vector frame including bloodstream vectors at a plurality of coordinates;
an interpolation processor that generates each interpolated frame by applying an interpolation process between two vector frames which are adjacent to each other, and that adds one or a plurality of interpolated frames between the vector frames; and
a particle calculator that derives a movement destination of each virtual particle of the bloodstream based on a frame array formed from a plurality of vector frames and a plurality of interpolated frames added between the vector frames.

2. The ultrasound diagnostic apparatus according to claim 1, wherein
the interpolation processor generates each of the interpolated frames formed from interpolated vectors at the plurality of coordinates by an interpolation process based on the bloodstream vector between two vector frames which are adjacent to each other.

3. The ultrasound diagnostic apparatus according to claim 1, wherein
the particle calculator calculates, based on the bloodstream vector of each particle in each frame included in the frame array corresponding to a plurality of time phases, a coordinate of the movement destination of the particle in a frame of a time phase later than the frame.

4. The ultrasound diagnostic apparatus according to claim 2, wherein
the particle calculator calculates, based on the bloodstream vector of each particle in each frame included in the frame array corresponding to a plurality of time phases, a coordinate of the movement destination of the particle in a frame of a time phase later than the frame.

5. The ultrasound diagnostic apparatus according to claim 3, further comprising:
a display processor that forms a bloodstream display image in which the coordinate of the movement destination of the particle over a plurality of time phases is shown in an image.

6. The ultrasound diagnostic apparatus according to claim 5, wherein
the display processor forms the bloodstream display image in which the coordinate of the movement destination of the particle over the plurality of time phases is shown by a trajectory by at least one of a point and a line.

7. The ultrasound diagnostic apparatus according to claim 6, wherein
in showing the trajectory of the particle over the plurality of time phases, the display processor sets different display forms between a trajectory portion of a time phase corresponding to a bright display period of the particle and a trajectory portion of a time phase corresponding to a period other than the bright display period.

8. The ultrasound diagnostic apparatus according to claim 7, wherein
the display processor sets a period from the time phase in which the trajectory of each particle is displayed to a time phase of a predetermined period in the past as the bright display period of the particle.

9. The ultrasound diagnostic apparatus according to claim 7, wherein
the display processor sets a period from the time phase in which each particle is generated to a time phase of a predetermined period later as the bright display period of the particle.

10. The ultrasound diagnostic apparatus according to claim 1, further comprising:
an image former that forms an ultrasound image of a heart including the bloodstream based on the signal obtained by transmitting and receiving ultrasound; and
a particle generator that generates a plurality of virtual particles of the bloodstream on a generation line connecting two characteristic points in the ultrasound image.

11. The ultrasound diagnostic apparatus according to claim 3, further comprising:
an image former that forms an ultrasound image of a heart including the bloodstream based on the signal obtained by transmitting and receiving ultrasound; and
a particle generator that generates a plurality of virtual particles of the bloodstream on a generation line connecting two characteristic points in the ultrasound image.

12. The ultrasound diagnostic apparatus according to claim 5, further comprising:
an image former that forms an ultrasound image of a heart including the bloodstream based on the signal obtained by transmitting and receiving ultrasound; and
a particle generator that generates a plurality of virtual particles of the bloodstream on a generation line connecting two characteristic points in the ultrasound image.

13. The ultrasound diagnostic apparatus according to claim 10, wherein
the two characteristic points are moved to follow a change of a shape of the heart in the ultrasound image formed over the plurality of time phases, so that the generation line follows a motion of the heart over the plurality of time phases.

14. The ultrasound diagnostic apparatus according to claim 11, wherein
the two characteristic points are moved to follow a change of a shape of the heart in the ultrasound image formed over the plurality of time phases, so that the generation line follows a motion of the heart over the plurality of time phases.

15. The ultrasound diagnostic apparatus according to claim 12, wherein
the two characteristic points are moved to follow a change of a shape of the heart in the ultrasound image formed over the plurality of time phases, so that the generation line follows a motion of the heart over the plurality of time phases.

* * * * *